United States Patent [19]
Condit et al.

[11] Patent Number: 5,363,661
[45] Date of Patent: Nov. 15, 1994

[54] METHOD AND APPARATUS FOR TESTING REFRIGERANT

[76] Inventors: David A. Condit, 45 Rockledge Dr., Avon, Conn. 06001; H. Harvey Michels, 7 Tumblebrook La., West Hartford, Conn. 06117; Thomas J. Garosshen, 90 Gilead Rd., Andover, Conn. 06232; Warren R. Clough, 6103 Owlwood Dr., Cicero, N.Y. 13039

[21] Appl. No.: 116,936

[22] Filed: Sep. 3, 1993

[51] Int. Cl.$^5$ .............................. G01N 31/00
[52] U.S. Cl. .................................. 62/77; 62/125; 62/129; 422/83; 422/86
[58] Field of Search ............... 62/77, 125, 127, 129, 62/298; 422/55, 56, 57, 83, 86; 436/124, 164, 166, 167, 192

[56] References Cited
U.S. PATENT DOCUMENTS

| | | | |
|---|---|---|---|
| 4,803,843 | 2/1989 | Otto | 62/127 X |
| 4,923,806 | 5/1990 | Klowdowski | 436/39 |
| 5,071,768 | 12/1991 | Klowdowski | 436/39 |
| 5,158,747 | 10/1992 | Manz et al. | 422/98 |
| 5,186,899 | 2/1993 | Drago et al. | 422/86 X |
| 5,237,873 | 8/1993 | Eichenlaub | 73/597 |
| 5,295,360 | 3/1994 | Olds et al. | 62/127 |

Primary Examiner—Harry B. Tanner

[57] ABSTRACT

A method and apparatus for testing refrigerant of one type for contamination by refrigerant of another type as would be the case if an air conditioning or refrigeration system charged with a non-chlorofluorocarbon refrigerant received a replenishment charge of a chlorofluorocarbon refrigerant. A sample of the suspected refrigerant mix is exposed to a reagent that will decompose the contaminant refrigerant but not the refrigerant that is proper for the system. The sample is then tested for a product of the decomposition. If the product is present, then one can conclude that the contaminant refrigerant is present.

20 Claims, 3 Drawing Sheets

METHOD AND APPARATUS FOR TESTING REFRIGERANT

BACKGROUND OF THE INVENTION

This invention relates generally to the field of vapor compression air conditioning and refrigeration systems. More specifically, the invention relates to a method, as well as an apparatus for practicing the method, for detecting the presence, as a contaminant, of one type of refrigerant in a system that uses another type of refrigerant.

A large proportion of the air conditioning systems in use today use chlorofluorocarbon (CFC) based refrigerants. There is, however, wide acceptance of the proposition that chlorine contributes to the destruction of the earth's ozone layer and that use of CFC-based refrigerants leads to the introduction of chlorine into the atmosphere. In an effort to slow or halt the rate of ozone depletion and in response to governmental mandates, manufacturers are using alternative refrigerants, containing less or no chlorine, in newer air conditioning systems. As a result, maintenance personnel are more and more likely to encounter air conditioning systems using non-CFC based refrigerants.

In general, one should not mix CFC and non-CFC based refrigerants in the charge of a single system. System materials compatible with one refrigerant type are frequently not compatible with another refrigerant type. For example, lubricating oils are commonly added to the refrigerant charge in a system to provide lubrication to system components such as the compressor. Lubricating oils suitable for use with CFC based refrigerants are not compatible with non-CFC based refrigerants. Use of the improper lubricating oil or charging a system with the incorrect refrigerant can lead to significant, even catastrophic, damage to the system.

The application with perhaps the highest potential for system damage due to charging with an improper refrigerant is in automotive air conditioning. The automotive industry is phasing out systems using CFC refrigerant R-12 in favor of systems using non-CFC refrigerant R-134a, both in newly manufactured systems and by conversion of existing systems. Newly manufactured automotive air conditioning systems bear prominent markings identifying the type of refrigerant used by the system but older systems do not. There is a greater likelihood that untrained and unqualified persons will attempt to service automotive air conditioning systems than other systems used in other applications. Charging R-12 into a system using R-134a can lead to component failures of such magnitude that repair may require replacement of the entire system. Charging R-134a into a system using R-12 can produce the same result.

Because of the increased possibility of system contamination by charging an improper refrigerant, there is a need for a way for maintenance personnel to detect such contamination as an aid in troubleshooting as well as to evaluate warranty claims. There is a concomitant need for an apparatus to practice the method. Such a refrigerant testing apparatus should be relatively inexpensive, simple to use and produce accurate results.

Although R-12 and R-134a differ in chemical composition, they are both colorless and their saturation temperatures and pressure characteristics are so similar that it is impossible, in a workshop environment, to distinguish between the two using such means as sight or pressure and temperature measurements. Some other method of distinguishing between the two is required.

SUMMARY OF THE INVENTION

The present invention is a method for detecting contamination of a CFC refrigerant by a non-CFC refrigerant or contamination of a non-CFC refrigerant by a CFC refrigerant as well as an apparatus that enables the practice of the method with a device that is compact, easy to use and inexpensive to make and operate.

There are two principles upon which the method and the operation of the apparatus is based. First, in the presence of certain reagents, a CFC refrigerant such as R-12 will decompose, producing decomposition products. There may be secondary chemical reactions leading to further decomposition products. The presence of one or more of these decomposition products can be indicated by a suitable indicator. The reaction conditions that cause the CFC refrigerant to decompose have no effect on non-CFC refrigerants such as R-134a.

Second, in the presence of hydroxyl (OH) radicals, a non-CFC refrigerant such as R-134a will decompose, producing hydrofluoric and/or trifluoracetic acid as decomposition products. The presence of an acid can also be indicated by a suitable indicator. The reaction conditions that cause the non-CFC refrigerant to decompose have no effect on CFC refrigerants such as R-12.

The apparatus of the present invention uses the above principles in a compact, portable and inexpensive package that includes a decomposition chamber in flow communication both with a source of refrigerant to be tested and with an indicator chamber having a suitable indicator. When a technician suspects that a system containing a CFC refrigerant is contaminated with a non-CFC refrigerant or that a system containing a non-CFC refrigerant is contaminated with a CFC refrigerant, he can connect a suitable embodiment of the apparatus to a charging connection in the system. System refrigerant then flows into the apparatus decomposition chamber where the suspected contaminant, if any, is decomposed into other chemical compounds, primarily acids. The decomposed refrigerant products flow from the decomposition chamber to an indicator chamber where it passes through a suitable indicator. The indicator will detect the presence of the decomposition product in the refrigerant and provide a display. A positive indication shows that there is contaminant refrigerant in the refrigeration system tested.

BRIEF DESCRIPTION OF THE DRAWINGS

The accompanying drawings form a part of the specification. Throughout the drawings, like reference numbers identify like elements.

DESCRIPTION OF THE PREFERRED EMBODIMENTS

Figure 1:
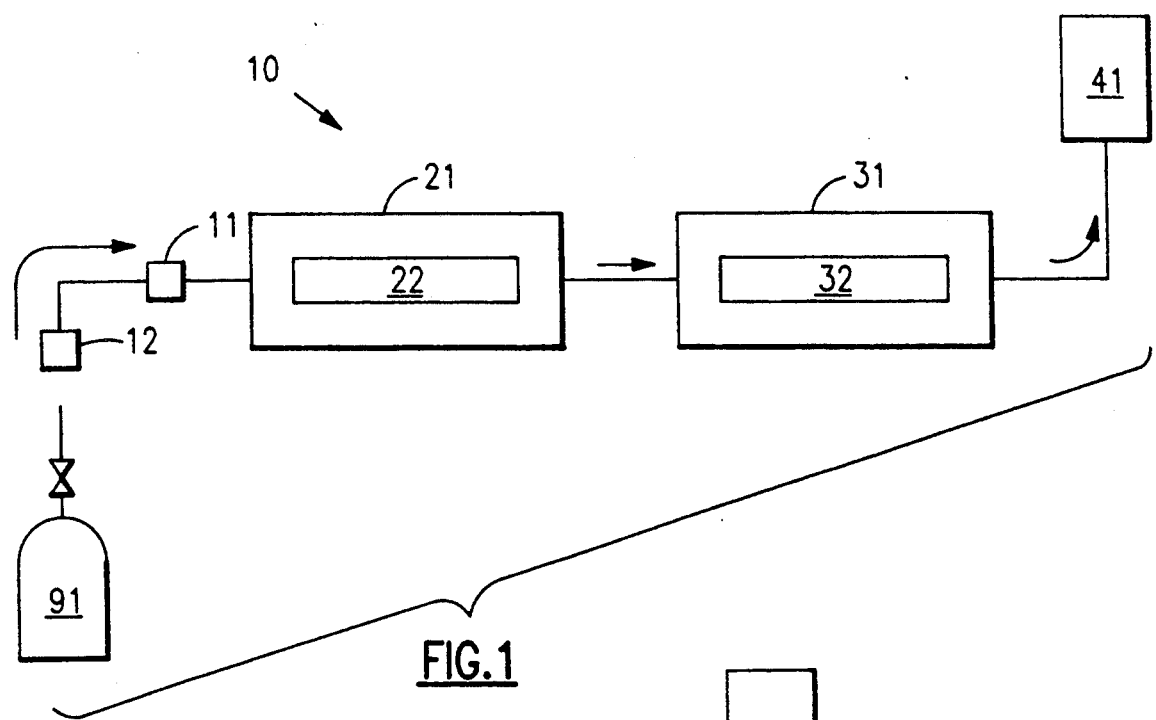
FIG. 1 is a schematic diagram that illustrates the principles underlying the apparatus of the present invention.

The chemical and physical processes for detecting CFC refrigerant R-12 ($CCl_2F_2$) as a contaminant in non-CFC refrigerant R-134a ($CF_3CH_2F$) are different from the processes for detecting contamination in the reverse situation. There are, however, similarities. These similarities allow for similar methods and apparatus to conduct tests in the two situations and for a single apparatus to be capable of conducting both tests with a minimum of modification.

Detection of Refrigerant R-12 as a Contaminant in Refrigerant R-134a

Refrigerant R-12 may be decomposed in at least three ways useful in the present invention:

1. Photodissociation. In the presence of ultraviolet light having a wavelength ($\gamma$) of 184.9 nanometers (nm), R-12 will dissociate as shown in the equation $$CCl_2F_2 + h\nu \rightarrow CClF_2 + Cl.$$

Ultraviolet light of $\gamma = 184.9$ nm does not decompose refrigerant R-134a.

Secondary reactions involving Cl and/or $CClF_2$ produce acids. As an example, $$2Cl + M \rightarrow Cl_2 + M,$$

where M is a third body collision partner such as a molecule of R-134a, and then $$Cl_2 + H_2O \rightarrow HOCl + HCl.$$

2. Thermal dissociation. At temperatures below 800° C., Refrigerant R-134a is thermally stable. At temperatures above 660° C., R-12 will decompose as shown in the equation $$2CCl_2F_2 \rightarrow 2CClF_2 + Cl_2.$$

The chlorine formed will react with water as in the reaction shown above to produce hypochlorous acid and hydrochloric acid.

3. Chemical decomposition. There are a number of chemical reagents that, while having no effect on R-134a, will, either alone or in the presence of catalysts and/or under certain physical conditions, cause R-12 to physically decompose. For example, R-12 will react with antimony trifluoride (Swarts reagent) as shown in the reactions $$CCL_2F_2 + SbF_3 \rightarrow CClF_3 + SbClF_2 \rightarrow CF_4 + SbCl_2F.$$

After the R-12 is decomposed in one of the above processes, the direct or secondary decomposition products resulting, for example, from hydrolysis can be detected by a suitable acid indicator.

Detection of Refrigerant R-134a as a Contaminant in Refrigerant R-12

There are several reactions that will produce hydroxyl radicals examples of which include:

1. In the presence of ultraviolet light having $\gamma = 254$ nm, aqueous hydrogen peroxide will dissociate as shown in the equation $$H_2O_2 + h\nu \rightarrow 2OH.$$

2. In the presence of ultraviolet light having $\gamma = 184.9$ nm, water will dissociate as shown in the equation $$2H_2O + h\nu \rightarrow 2OH + H_2.$$

3. In the presence of microwave energy, hydrogen will dissociate into free hydrogen which will then react with nitrogen dioxide as shown in the equations $$H_2 + h\nu \rightarrow 2H$$

and $$H + NO_2 \rightarrow NO + OH.$$

4. In the presence of ultraviolet light having $\gamma < 280$ nm, nitric acid will dissociate as shown by the equation $$HNO_3 + h\nu \rightarrow NO_2 + OH.$$

Refrigerant R-12 does not react with hydroxyl radicals. Refrigerant R-134a, however, does react with OH to produce tetrafluoroethyl radicals and water as shown in the equation $$CF_3CH_2F + OH \rightarrow CF_3CHF + H_2O.$$

The $CF_3CH_2$ radical reacts further to produce trifluoroacetic acid and hydrofluoric acid, as shown in the equation $$CF_3CHF + OH, H_2O \rightarrow CF_3C(O)OH, HF, F^-, H_3O^+,$$

other products.

After the R-134a is decomposed in one of the above processes, the decomposition products can be detected by a suitable acid indicator.

The above principles allow one to determine the presence of a contaminating refrigerant of one type in a refrigerant of another type both when the contaminant is a CFC refrigerant in a non-CFC refrigerant and when the contaminant is a non-CFC refrigerant in a CFC refrigerant. To determine the presence of a contaminant, one draws a sample of refrigerant from a source of supply of the refrigerant such as an air conditioning or refrigeration system or a replenishment cylinder. The sample is then exposed to a reagent that, under conditions appropriate to the refrigerant and the reagent, will cause the decomposition of the suspected contaminant. The sample is then tested for the presence of a telltale product of decomposition. If the test shows the presence of the product of decomposition, then one can conclude that the source of refrigerant is contaminated by refrigerant of a non-compatible type.

FIG. 1 depicts schematically an apparatus that embodies the teachings of the present invention. The figure shows testing apparatus 10 in position to be attached to refrigerant source 91. Fitting 12 connects apparatus 10 to source 91. When connected, refrigerant flows from source 91 through flow limiting device 1 into decomposition chamber 21. Reagent 22 is located in chamber 21. Reagent 22 is chosen so as to be nonreactive with refrigerant that is proper for the source being tested but to decompose refrigerant of the improper type. Thus refrigerant flowing into indicator chamber 31 may contain a product of the decomposition of a contaminating refrigerant if source 91 is contaminated. Indicator 32 is located in chamber 31. Indicator 32 may be of any suitable type that will detect and indicate the presence of a decomposition product of the contaminating refrigerant.

A colorimetric indicator is simple and convenient for this use. Such an indicator comprises a bed of a substance through or over which a fluid to be tested may flow. The substance is chosen so that it will react with the component of the fluid it is desired to detect to produce a change in color in the bed. Thus, in this case, a color change in the bed is indicative of the presence of the refrigerant decomposition product. It must, of course, be possible to observe the indicator bed to determine a change in color. This can be accomplished by making indicator 32 so that it can be removed from chamber 31 for reading, providing a window in a wall of chamber 31 or simply making the wall of the chamber transparent.

From chamber 31, the refrigerant flows into collector 41 where the refrigerant effluent is stored for disposal.

Figure 2A:
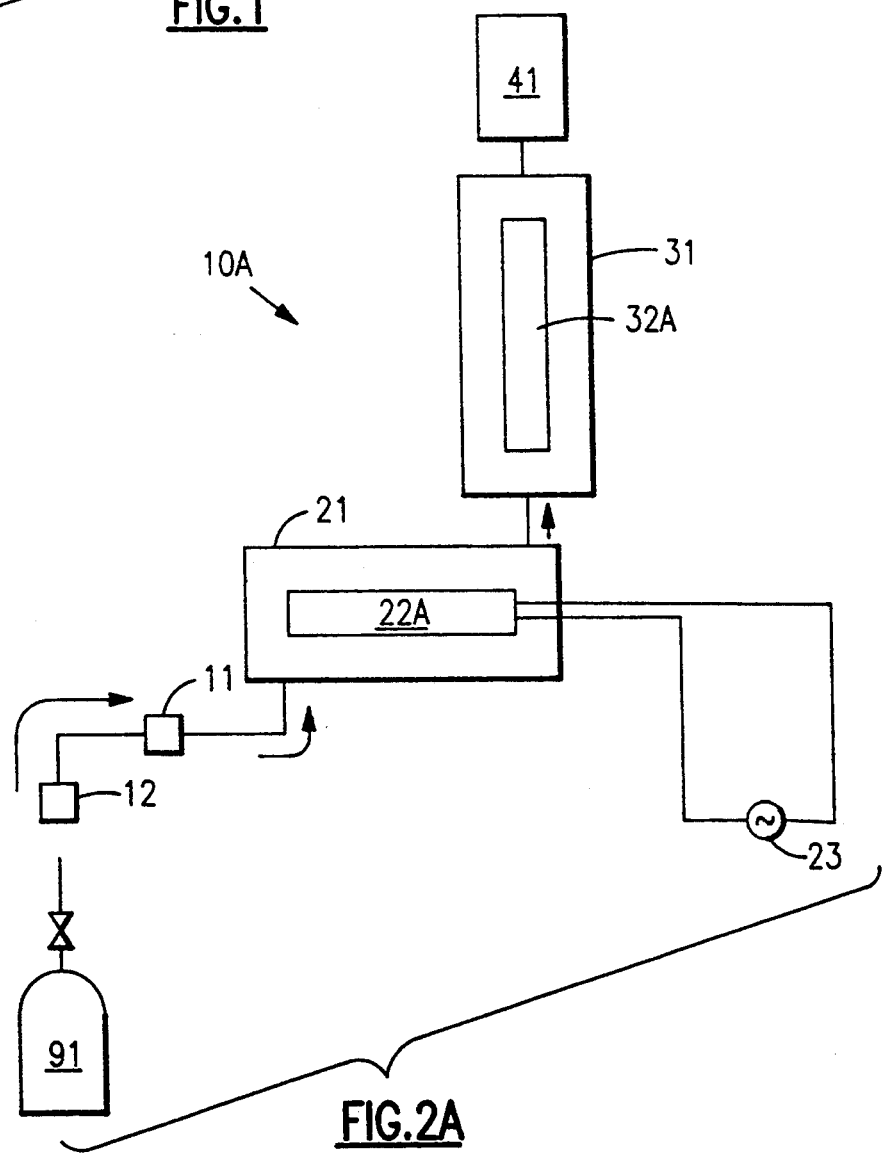
FIGS. 2A, 2B, and 2C are schematic diagrams of different embodiments of the apparatus of the present invention.
Figure 2C:
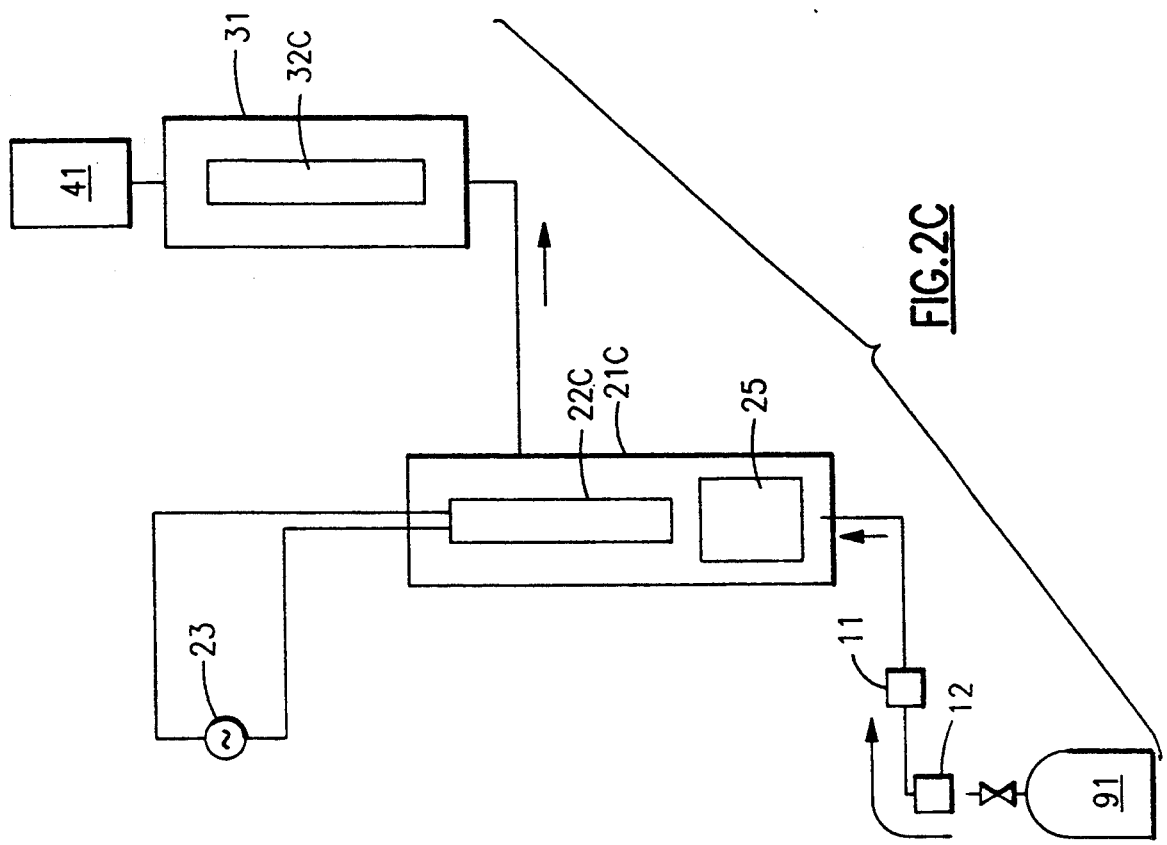
Figure 2B:
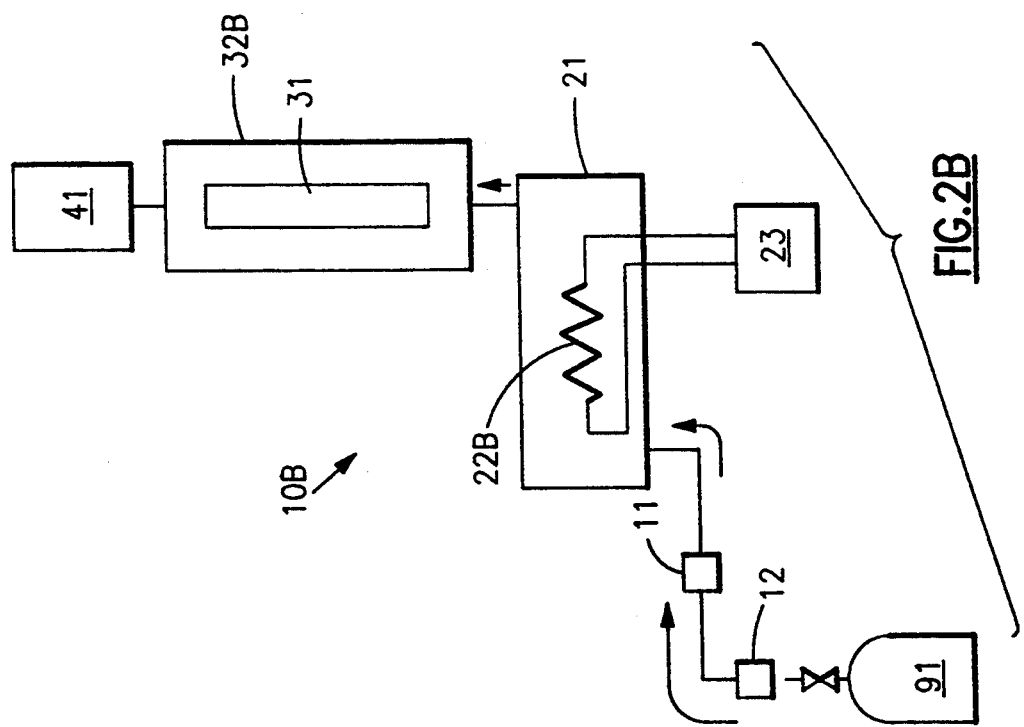

FIGS. 2A, 2B, and 2C more specifically depict schematically different embodiments of the testing apparatus of the present invention that take advantage of the various phenomena discussed above to detect refrigerant contamination. In those figures, features that are unique to a particular embodiment have reference identifiers with letter suffixes that correspond to the letter suffix of the figure identifier. Features that are the same as corresponding features in FIG. 1 have reference identifiers without letter suffixes.

FIG. 2A shows testing apparatus 1 OA for the detection of refrigerant R-12 as a contaminant in refrigerant R-134a. The reagent in this embodiment is ultraviolet lamp 22A, which receives its power from power supply 23. As discussed above, R-12, in the presence of ultraviolet light having a $\gamma = 184.9$ nm, decomposes, with two decomposition products being hypochlorous and hydrochloric acids. Indicator 32A in indicator chamber 3 1 therefore is of a type that will detect the presence of acids and preferably is a colorimetric indicator.

FIG. 2B shows another testing apparatus, 10B, for the detection of refrigerant R-12 as a contaminant in refrigerant R-134a. The reagent in this embodiment is heat provided by heating element 22B, located in decomposition chamber 21 and powered by power supply 23. Under properly elevated temperatures, R-12 decomposes as discussed above. Indicator 32B in chamber 31 therefore is of a type that will detect the presence of acids and preferably is a colorimetric indicator.

FIG. 2C shows testing apparatus 10C for the detection of refrigerant R-134a as a contaminant in refrigerant R-12. There are two elements located in decomposition chamber 22, which chamber also contains a source of hydroxyl radicals such as hydrogen peroxide. Element 25C is a gas effusion device for saturating the source of OH radicals with the refrigerant. Lamp 22C receives power from power supply 2 3 and emits ultraviolet light having a $\gamma = 254$ nm. Because R-12 decomposes when exposed to ultraviolet light having a $\gamma = 184.9$, it is important that lamp 22C not emit light of the shorter wavelength. This is easily accomplished and lamp 22A and lamp 22C may be identical with the exception of fitting lamp 22C with a filter that allows only ultraviolet light of the desired wavelength to pass, Alternatively, element 25 can be made to be integral with lamp 22C to produce hydroxyl radicals which are then injected into a flowing refrigerant stream. In this configuration, lamp 25C could emit ultraviolet radiation at $\gamma = 184.9$ since the refrigerant is screened from ultraviolet radiation by element 25. As discussed above, acids are secondary decomposition products of R-134a. Indicator 32C in chamber 31 is therefore of a type that will detect the presence of acids and preferably is a colorimetric indicator.

Figure 3:
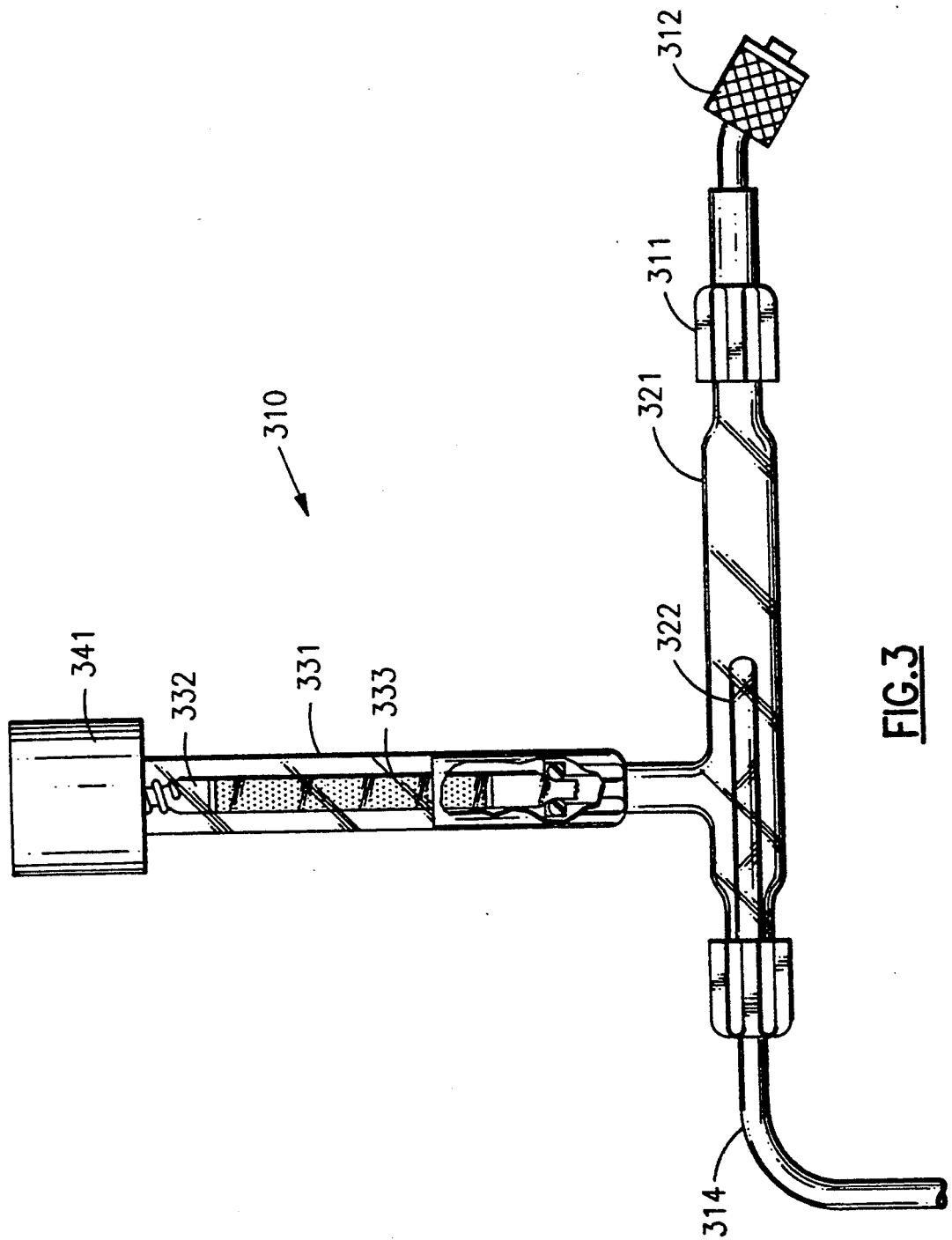
FIG. 3 is an elevation view of one embodiment of the apparatus of the present invention.

FIG. 3 is an elevation view of an apparatus for testing for refrigerant R-12 contamination in refrigerant R-134a that embodies the teaching of the present invention. Refrigerant flows into apparatus 310 through connector 312, a Schrader ® fitting of the type that will mate with the Schrader ® charging valve found on nearly all air conditioning and refrigeration systems. Coupling 311 contains an orifice as a flow limiting device. Decomposition chamber 321 contains lamp 322 that emits ultraviolet light having $\gamma = 184.9$ nm. Power cord 314 supplies power to lamp 322 from a power supply (not illustrated). Inside indicator chamber 331 is indicator tube 332 that contains colorimetric indicating medium 333. Collector 341 collects refrigerant that passes through apparatus 310 for later disposal.

The wall of indicator chamber 331 is made of a transparent material such as plastic. Indicator tube 332 is made of transparent glass or plastic. Indicating medium 333 is therefore visible through chamber 331 and tube 332.

Indicator tube 332 can be the same or similar to the tube described in U.S. Pat. 4,923,806, issued May 8, 1990 to Klowdowski and assigned to the same assignee as the present invention. The '806 patent covers the TOTALTEST ® refrigerant testing device now in widespread use. The tube of the '806 patent and used in the TOTALTEST ® device contains two colorimetric indicators, one that indicates the presence of water in a refrigerant sample and one that indicates the presence of acid. The acid indicating medium in the '806 tube is bromophenol blue on a glycerol film coating a silica sand base. The medium is initially blue in color. In contact with acid, the medium turns a purple or purplish pink color. The apparatus of the present invention does not use the moisture detecting capability of the '806 tube but the presence of the moisture indicating medium does not adversely impact on the tube's use in the apparatus. Alternatively, indicator tube 322 could be specially made for use in the apparatus of the present invention and have, as illustrated in FIG. 3, only a single bed of indicating medium. During manufacture of the '806 tube, the tube ends are heated and drawn to a close to seal the indicating media from exposure to air.

To test a sample of refrigerant R-134a for contamination by refrigerant R-12 using apparatus 310 and an indicating tube having a bromophenol blue indicating medium, the test operator first breaks the ends off indicator tube 322 and inserts the tube into indicator chamber 331. Then the operator connects apparatus 310 to a source of the refrigerant to be tested by means of connector 312 and energizes lamp 322. With apparatus us 310 connected to the refrigerant source, a sample of refrigerant flows from the source through connector 312 and coupling 311 into decomposition chamber 321. There, refrigerant R-12 present in the sample will decompose when exposed to ultraviolet light from lamp 322. The refrigerant sample then enters indicating chamber 331 and flows through indicator tube 332, where it passes through and contacts indicating medium 333. If there is refrigerant R-12 in the sample flow, the acidic decomposition products of that refrigerant will react with indicating medium 333 to produce a color change in the medium.

Apparatus 310 can be quickly and easily converted to test refrigerant R-12 for contamination by refrigerant R-134a by either replacing lamp 322 with a lamp that emits ultraviolet light of the proper wavelength or installing a filter on the existing lamp and by providing a source of hydroxyl ions in decomposition chamber 321.

As discussed in the '806 patent, acid can be present in a refrigerant from several sources, primarily the decomposed insulation of an overheated compressor motor. If an acid indicating medium is used to detect the presence of refrigerant decomposition products, acid from other sources could produce a false positive indication of contamination. Therefore, before conducting a test for contamination of one refrigerant type by another refrigerant type, one should first determine that the refrigerant to be tested is free of acid. The TOTALTEST® device can be used for that determination or apparatus 310 can be used with lamp 322 deenergized to prevent refrigerant decomposition.

We claim:

1. A method of testing a refrigerant that should be a pure first refrigerant compound for the contaminating presence of a second refrigerant compound comprising the steps of:
   withdrawing a sample flow of said refrigerant from a closed system containing refrigerant;
   causing said sample flow to come in contact with means for decomposing said second refrigerant compound; and
   testing said sample flow by causing it to come in contact with means for indicating the presence of a decomposition product of said second refrigerant compound, a positive indication of the presence of said decomposition product being indicative of contamination of said refrigerant by said second refrigerant compound.

2. The method of claim 1 further comprising the step, performed after said withdrawing step and before said causing step, of:
   reducing the pressure of said sample flow.

3. An apparatus (10) for testing a refrigerant that should be a pure first refrigerant compound for the contaminating presence of a second refrigerant compound comprising:
   means (12) for withdrawing a sample flow of said refrigerant from a closed system (91) containing refrigerant;
   means (21), in downstream flow relationship with said withdrawing means, for causing said sample to come in contact with means (22, 25C) for decomposing said second refrigerant compound; and
   means (31, 32), in downstream flow relationship with said causing means, for indicating the presence of a decomposition product of said second refrigerant compound, a positive indication of the presence of said decomposition product being indicative of contamination of said refrigerant by said second refrigerant compound.

4. The apparatus of claim 3 further comprising:
   means (11), in downstream flow relationship with said withdrawing means and in upstream flow relationship with said causing means, for reducing the pressure of said sample flow.

5. The apparatus of claim 3 in which said pressure reducing means comprises an orifice.

6. The apparatus of claim 3 further comprising:
   means (41), in downstream flow relationship with said testing means, for collecting said sample flow.

7. The apparatus of claim 3 in which said withdrawing means comprises:
   a fitting (312) adaptable to connection to a test/charging fitting in said closed system.

8. The apparatus of claim 3 in which said causing means comprises:
   a decomposition chamber (32).

9. The apparatus of claim 3 in which said decomposing means comprises:
   an ultraviolet lamp (22A).

10. The apparatus of claim 9 in which said lamp emits ultraviolet energy having a wavelength of 184.9 nm 11. The apparatus of claim 9 in which said decomposing means comprises:
    an ultraviolet lamp (22C) that emits ultraviolet energy having a wavelength of 254 nm and
    means (25C) for producing hydroxyl ions.

12. The apparatus of claim 3 in which said indicating means comprises:
    bromophenol blue in a glycerol film coating a silica sand base.

13. The apparatus of claim 3 in which said indicating means comprises:
    a transparent tube having disposed within it a contaminant indicating substance adapted to indicating the presence of a refrigerant decomposition product.

14. The apparatus of claim 13 in which said contaminant indicating substance comprises:
    bromophenol blue in a glycerol film coating a silica sand base.

15. An apparatus for testing a refrigerant that should be pure refrigerant R-134a for the contaminating presence of refrigerant R-12 comprising:
    means (312) for connecting said apparatus to a source of refrigerant to be tested;
    means (311), in downstream flow relationship with said connecting means, for reducing the pressure of said refrigerant;
    a decomposition chamber (321) in downstream fluid flow relationship with said pressure reducing means;
    a lamp capable of emitting ultraviolet energy having a wavelength of 184.9 nm located in said decomposition chamber; and
    a contaminant indicator holder assembly (331) in downstream fluid flow relationship with said decomposition chamber.

16. The apparatus of claim 15 further comprising:
    a transparent tube (332) having disposed within it a contaminant indicating substance (333) adapted to indicating the presence of a refrigerant decomposition product.

17. The apparatus of claim 15 in which said contaminant indicating substance comprises:
    bromophenol blue in a glycerol film coating a silica sand base.

18. An apparatus for testing a refrigerant that should be pure refrigerant R-12 for the contaminating presence of refrigerant R-134a comprising:
    means (12) for connecting said apparatus to a source of refrigerant to be tested;
    means (11), in downstream flow relationship with said connecting means, for reducing the pressure of said refrigerant;
    a decomposition chamber (21) in downstream fluid flow relationship with said pressure reducing means;

a lamp (22C) capable of emitting ultraviolet eneraby having a wavelength of 254 nm located in said decomposition chamber;

means (25C) for producing hydroxyl ions located in said decomposition chamber; and a contaminant indicator holder assembly (31) in downstream fluid flow relationship with said decomposition chamber.

19. The apparatus of claim 18 further comprising:

a transparent tube (332) having disposed within it a contaminant indicating substance (333) adapted to indicating the presence of a refrigerant decomposition product.

20. The apparatus of claim 19 in which said contaminant indicating substance comprises:

bromophenol blue in a glycerol film coating a silica sand base.

* * * * *